United States Patent [19]

Sramek

[11] 4,191,962
[45] Mar. 4, 1980

[54] LOW COST MULTI-CHANNEL RECORDER AND DISPLAY SYSTEM FOR MEDICAL AND OTHER APPLICATIONS

[76] Inventor: Bohumir Sramek, 19211 Edgehill Dr., Irvine, Calif. 92715

[21] Appl. No.: 943,777

[22] Filed: Sep. 20, 1978

[51] Int. Cl.² ............................................. A61B 5/04
[52] U.S. Cl. ............................ 346/110 R; 128/712; 354/76; 354/105; 358/244
[58] Field of Search ............... 128/710, 712; 358/254, 358/244; 346/110 R, 33 ME; 354/105, 76

[56] References Cited

U.S. PATENT DOCUMENTS

| | | | |
|---|---|---|---|
| 3,111,887 | 11/1963 | Alexander | 346/110 R |
| 3,277,240 | 10/1966 | Marjoram | 358/244 |
| 3,434,151 | 3/1969 | Bader | 128/712 |
| 3,707,147 | 12/1972 | Sellers | 128/712 |
| 3,906,522 | 9/1975 | Carroll | 354/105 |

*Primary Examiner*—Howard W. Britton

*Attorney, Agent, or Firm*—Knobbe, Martens, Olson, Hubbard and Bear

[57] ABSTRACT

A system for electronically representing in wave form plural physiological phenomena, viewing this representation, and simultaneously obtaining a labeled permanent photographic record of the representation. While of general application, the system has particular utility in low-cost medical observance and recordation of electrocardiogram wave forms. The data from the patient is presented on the cathode ray tube of an oscilloscope. This representation is viewed via an assembly of mirrors by the observer and simultaneously by a camera. When the observer is content with the output, he activates the camera which takes a permanent picture of the wave forms displayed on the cathode ray tube. The camera shutter is synchronized with the cathode ray tube display such that the shutter is held open for one complete sweep of the electron beam.

11 Claims, 11 Drawing Figures

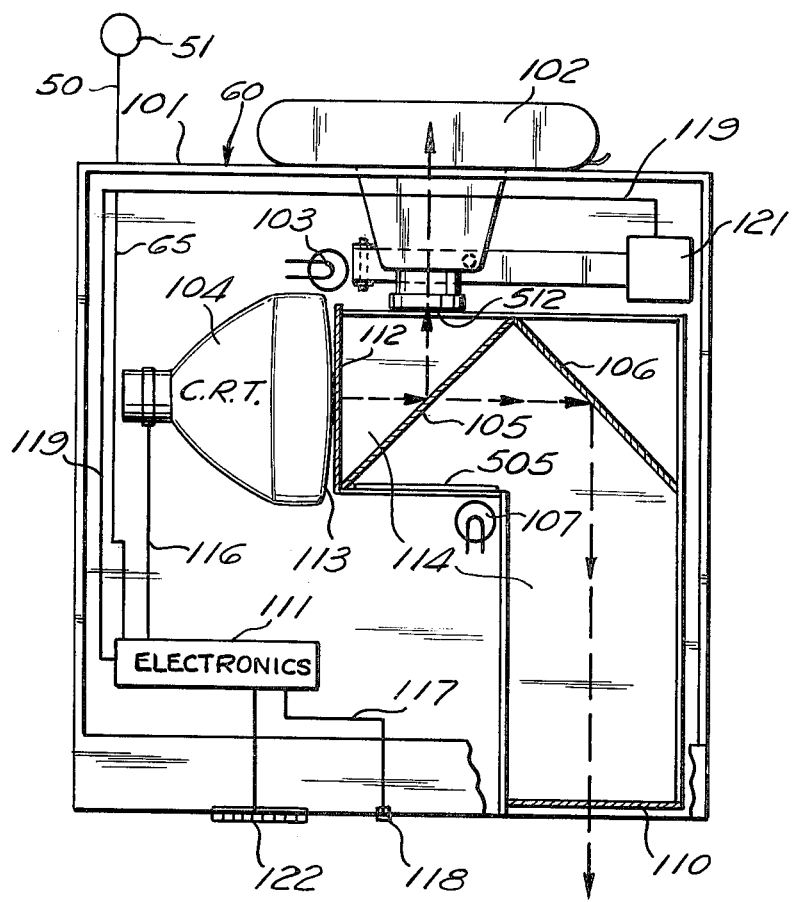
Fig. 1
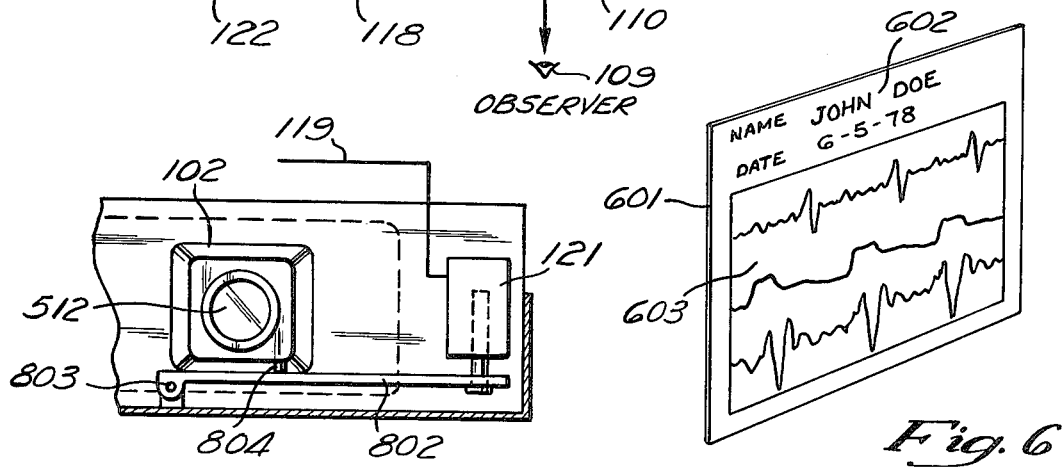
Fig. 8
Fig. 6

LOW COST MULTI-CHANNEL RECORDER AND DISPLAY SYSTEM FOR MEDICAL AND OTHER APPLICATIONS

BACKGROUND OF THE INVENTION

The strip chart recorder, widely used for diagnostic display, is uneconomical in time and money. Thus, low-cost single channel electrocardiograms (ECG) units typically require 12 consecutive measurements with the appropriate labeling of each strip chart output (6 for extremities and 6 for chest leads). The more expensive multi-channel units save time in taking and labeling the strip chart output, but are considerably more expensive. Also, the strip chart output is often of such length that its storage is cumbersome.

In either the single channel or the multi-channel ECG units, the strip chart recorder utilizes mechanical means (motors, gears, etc.) to permanently record; thus, such units are susceptible to environmental influences, and are expensive to manufacture and maintain.

SUMMARY OF THE INVENTION

In the preferred embodiment, the invention receives physiological data and electronically represents an image of this data on a cathode ray tube. By means of a see-through mirror, the image from the cathode ray tube is split into two identical full images. One of these images is reflected to an observation window by a second mirror while the second image is directed to a Polaroid or other camera. When the observer is satisfied that the data is representative of the conditions, the observer activates the camera shutter which takes a picture of the image on the cathode ray tube along with a label containing such information as number, date and name of patent.

The present invention offers several important advantages over the prior art. It has a minimal number of mechanical components and its electronic and photographic components are reliable, relatively inexpensive, and highly accurate with increased bandwidth. Use of an instant type camera such as manufactured by the Polaroid Corporation permits a virtually instantaneous permanent record which, if unsatisfactory for any reason, can be retaken without additional set-up time. Also, unlike the prior art strip chart recorder, no recording paper is wasted during set-up.

The cathode ray tube display allows multiple wave forms to be displayed simultaneously, thus providing a substantial saving of operator time.

Another significant feature of the invention is that it allows continuous observation of the wave form display before and during the photographic recording so that the operator may be assured that the wave form is of the requisite quality and stability.

Still another feature of the invention is that it incorporates electronic means which enable the automatic exposure of a single complete frame regardless of when the operator pushes the start or take button.

BRIEF DESCRIPTION OF THE DRAWINGS

FIG. 1 is a horizontal elevation overall view of a multi-channel recorder and display system constructed in accordance with the invention;

FIG. 6 illustrates a photographic recording produced by the system;

FIG. 8 illustrates the mechanical layout of the shutter activator mechanism.

DETAILED DESCRIPTION OF THE INVENTION

Referring to FIG. 1, input data on input lead 50 is produced by an electrical transducer probe 51. Typically, probe 51 is attached to a patient for producing electrical signals representative of physiological phenomena. Lead 50 is connected to terminals on the rear of the multi-channel recorder and display system 60 having an outer enclosure 101.

Figure 5A:
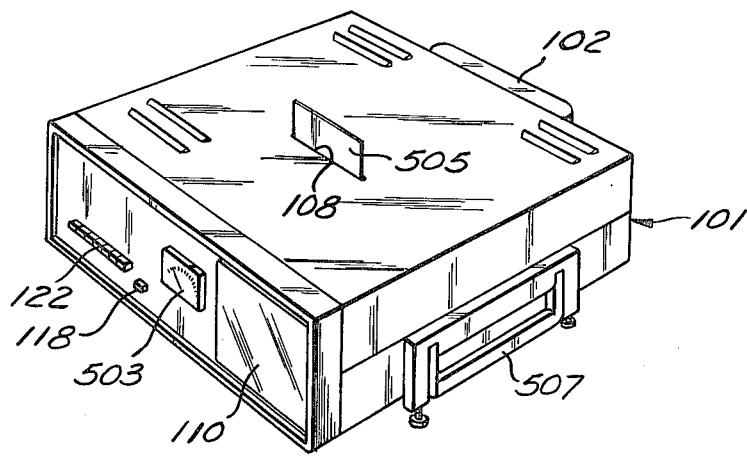
FIGS. 5A, 5B and 5C are perspective views of the overall system, FIG. 5A showing the front, top and left hand sides of the external cabinet, FIG. 5B showing the top, front and left hand sides with the top cover removed and FIG. 5C showing the top, rear and left hand sides with the top cover removed.
Figure 5B:
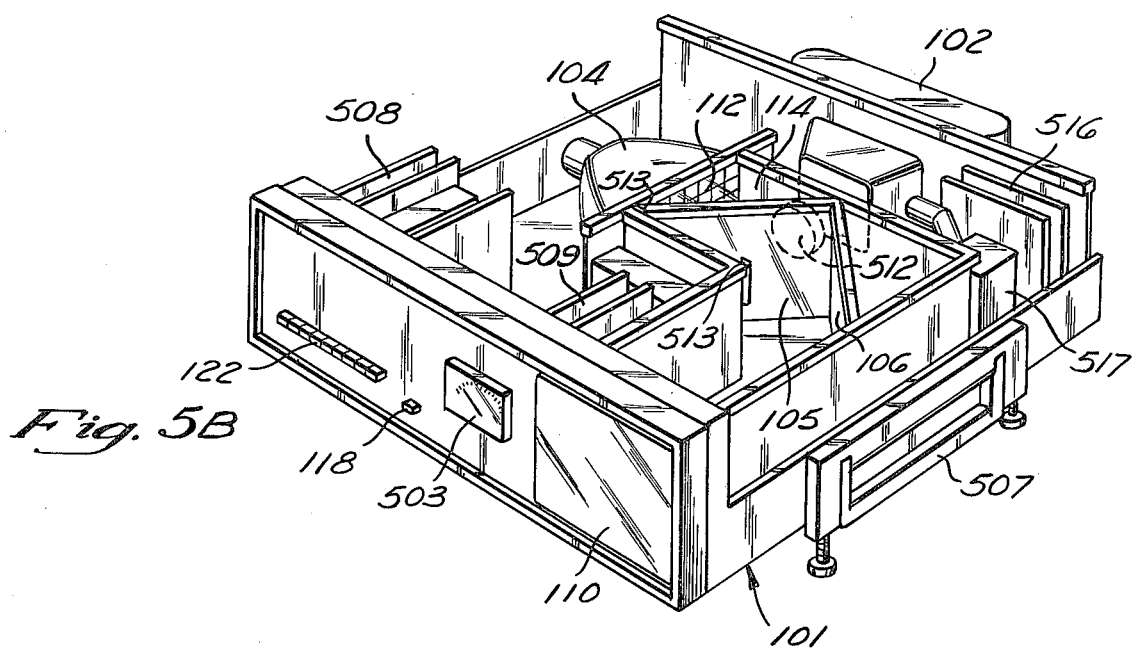
Figure 5C:
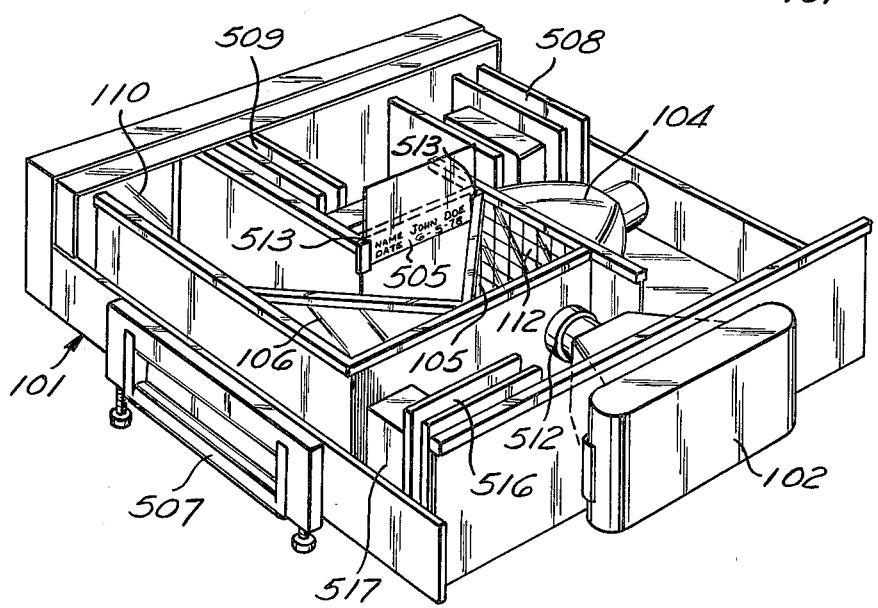

Enclosure 101 is best illustrated in FIGS. 5A–C. As shown, this enclosure includes a carrying handle 507. Interior of this enclosure, electrical lead 65 carries the input data to the electronic control circuitry 111. It will be understood that plural probes 51 may be connected to various places upon the patient so as to provide several independent channels of input data into the system 60. One or more of such data channels are selected by means of mode switches 122 to produce a display wave form, corresponding to each data channel, upon an oscilloscope including cathode ray tube (CRT) 104. CRT 104 is driven by the electronic control circuitry 111 via drive lead 116.

As shown in FIGS. 1, 5B and 5C, the image produced on the screen 113 of the cathode ray tube 104 passes into an optical channel 114, including a two-way mirror 105 mounted at a 45° angle with respect to the screen of the tube 104. Mirror 105 both reflects the cathode ray tube image into the lens 512 of camera 102, mounted at a 90° angle with respect to screen 113, and also passes the light rays as shown to a second mirror 106, mounted at a 90° angle with respect to mirror 105. Mirror 106 reflects the CRT image through a gray filter 110 to an observer 109 facing the front of the system enclosure 101. Grey filter 110 both provides a protective enclosure at the end of the optical channel 114 and attenuates ambient light into the optical channel 114 to improve the contrast of the CRT screen image seen by the observer. In addition, the walls of the channel 114 are advantageously coated black to prevent optical interference.

A grid 112 suitably engraved in a glass sheet or like transparent medium is side lit by lamp 103 so as to provide an overlaid rectangular grid for the output wave forms displayed upon the CRT screen 113.

A permanent recording of the displayed wave form is obtained by actuating start switch 118, connected to the electronic control circuitry 111 via line 117. Automatic electronic control means, explained in detail hereinafter, activates the camera shutter control solenoid 121 via line 119, for recording on film a single complete horizontal sweep of the electron beam across the screen 113 of the cathode ray tube.

The top of the enclosure 101 further includes a slot 108 (as shown in FIG. 5A) for receiving a transparent film 505 (FIG. 5C) or other identifying medium framing a mat surface on which may be written identifying information. Thus, the observer 109 will normally desire to permanently record on the photograph, simultaneous with photographically recording the displayed wave forms, such information as the name of the patient and date of recording. Film 505 is slidably retained by guides 513 (FIG. 5C) and illuminated from behind by lamp 107 so that the camera photographs both the CRT displayed wave forms reflected by the mirror 105 and the information written on the mat film which is seen by the camera through the two-way mirror 105.

Typically, the electronic components will be mounted to the housing or upon printed circuit boards slidably retained by the housing within the enclosure 101. Thus, referring to FIGS. 5B and 5C, the control electronic circuitry 111 is mounted upon the circuit boards 508. The low voltage power supply for the control circuitry 111 is mounted upon circuit boards 509 and the high voltage power supply circuitry for driving the CRT tube 104 is mounted on circuit boards 516 and to the chassis in close proximity to the boards 516, as shown by component 517. A meter 503 mounted upon the face of the front panel indicates line voltage level and/or other circuit voltages or currents.

Figure 2:
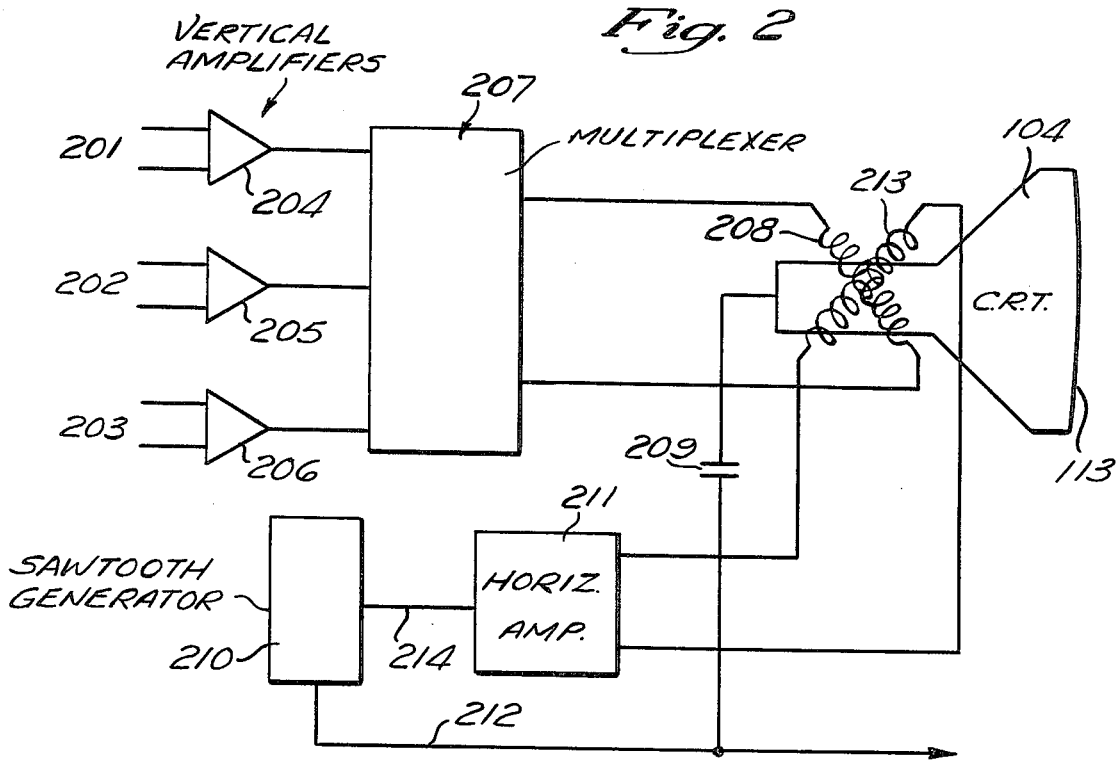
FIG. 2 is a block diagram of the electronic circuitry used for driving the cathode ray tube display.

The manner in which multiple wave forms are displayed on the cathode ray tube 104 is illustrated in FIG. 2. Three input channels 201, 202 and 203 of data information are connected to the inputs of respective vertical amplifiers 204, 205 and 206. The particular channels connected to these vertical amplifiers are in turn determined by the channel select push-buttons 122. The outputs of the vertical amplifiers are connected to the input of a multiplexer 207, which drives the vertical deflection yoke 208 of the cathode ray tube 104. As is well known in the art, vertical deflection yoke 208 controls the vertical position of the electron beam upon the CRT screen 113.

Figure 3:
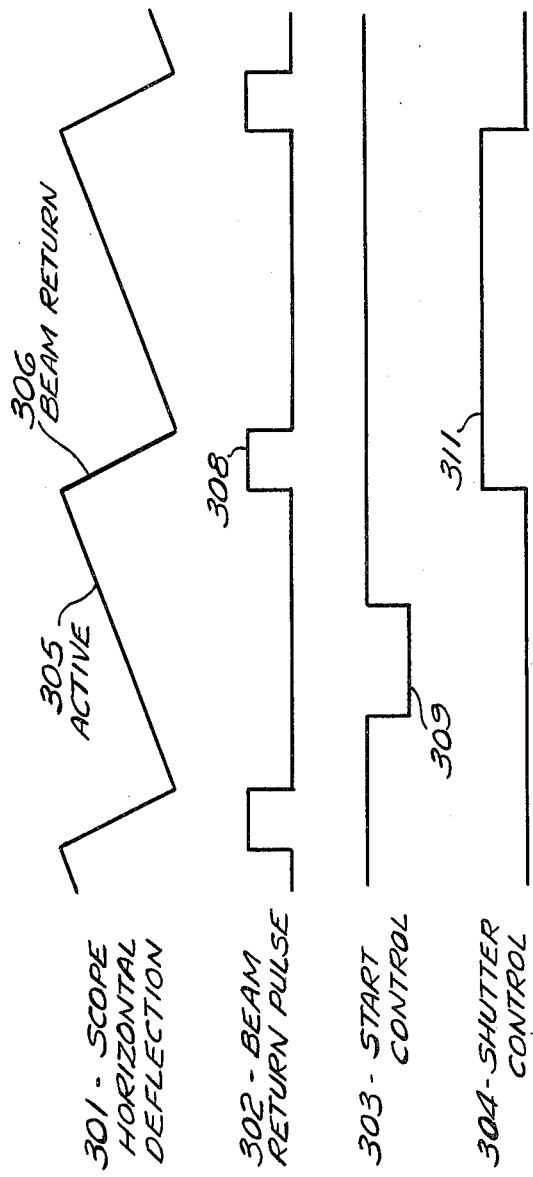
FIG. 3 illustrates wave forms showing the time relationships between the horizontal deflection of the cathode ray tube, the beam return pulse, the activation of the start button, and the shutter control signal.

CRT tube 104 also includes a horizontal sweep circuit comprising a saw-tooth generator 210 coupled to horizontal amplifier 211 which drives the horizontal sweep deflection yoke 213. This yoke 213 controls the horizontal position of the electron beam upon the CRT screen 113. The horizontal deflection wave form is shown at 301 in FIG. 3. During the active mode 305, the electron beam is deflected from a starting point at one edge of the screen across the screen 113. At the end of this horizontal sweep, the beam return wave form 306 returns the beam to its starting point. During this beam return interval, a beam return or "blanking" pulse wave form 302 is produced. This blanking pulse 308 is supplied on lead 212 through capacitor 209 to turn off the electron beam so that the return trace does not appear on the CRT screen 113.

Wave forms are conventionally displayed on a CRT screen by sweeping the beam from left to right across the screen. It will be noted that mirror 106 in the preferred embodiment of FIGS. 1 and 5 reverses the horizontal image of the cathode ray tube such that the left side of the face 113 of the cathode ray tube appears on the right side of window 110. This reversal is easily accommodated by the electronics 111, which cause the cathode ray tube to sweep from right to left, such that to an observer, it appears that the wave forms are displayed in their conventional form.

Figure 4:
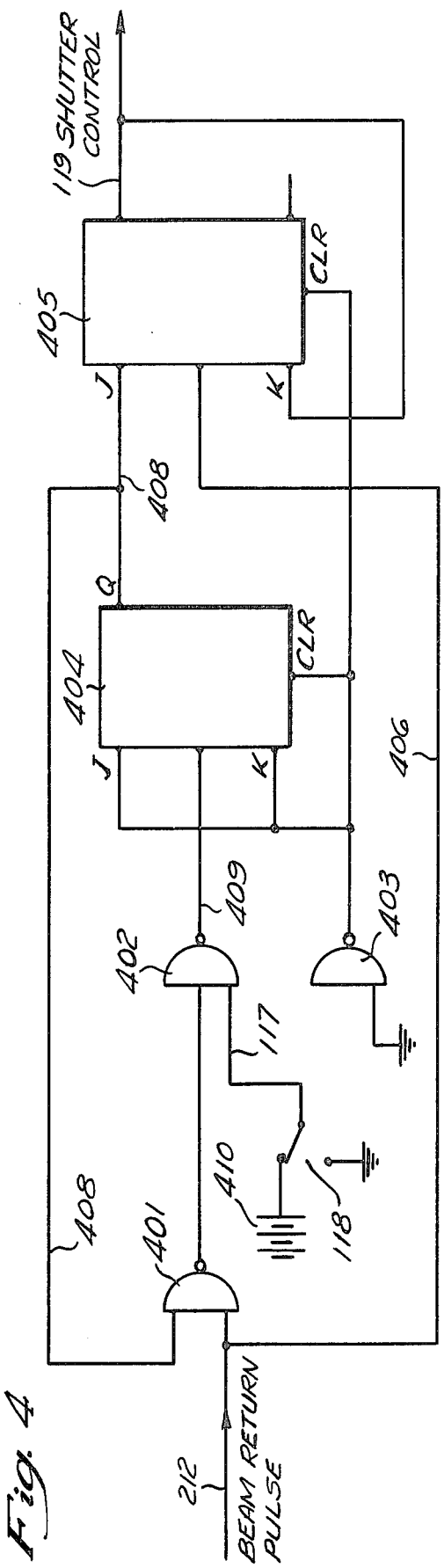
FIG. 4 is an electrical schematic of the automatic shutter control.

The shutter control circuitry is shown in FIG. 4. As shown by start control wave form 303 in FIG. 3, the start control pulse 309 (produced by actuating push-button 118) may occur at any time during the horizontal sweep. However, it will be apparent from FIG. 3 that if the shutter was triggered in time coincidence with pulse 309, the shutter could be opened at any time during the active wave form 305. The circuitry of FIG. 4 determines that the shutter is always opened only at the beginning of the horizontal sweep and closed at the end of the horizontal sweep by a shutter control signal 311 shown by wave form 304 of FIG. 3.

In its non-actuated state, start switch 118 connects one input of 402 via line 117 to a voltage potential source 410. When actuated, the push-button connects this input to ground. The other input of gate 402 is connected to the output of a gate 401, whose input in turn are the output lead 408 of flip-flop 404 and the beam return pulse 308 on lead 212. Beam return pulse 308 enables gate 401 at the beginning of each horizontal sweep cycle. However, gate 402 is blocked until such time as the start switch 118 is actuated to ground its input to gate 402. Gate 402 is then enabled upon the occurrence of beam return pulse 308, resulting in the triggering of flip-flop 404, which in turn triggers flip-flop 405 to generate a shutter control signal 311 on output lead 119. The tail end of this pulse 311 is provided by the next beam return pulse 308, which is supplied through lead 406 to trigger flip-flop 405 to its original state. Gate 403 acts as an inverter supplying a high state to the J. K and CLR inputs of flip-flop 404 and the CLR input of flip-flop 405.

It will thus be seen that the shutter control pulse 311 precisely coincides with a single complete horizontal sweep across the CRT immediately following actuation of the push-button 118.

The mechanism responsive to pulse 311 for driving the camera shutter is shown in detail in FIG. 8. The solenoid 121 is driven by shutter control lead 119. The solenoid actuator is connected to a lever arm 802 pivotally mounted at its opposite end 803. Lever 802 abuts the camera shutter button 804 such that when the solenoid is actuated, the lever 802 rotates upwardly a predetermined distance to open the shutter for the requisite time. It will be understood that the shutter is set to its Bulb position so that the camera shutter opens and closes coincident with the actuation of the camera shutter button 804.

A representative permanent record produced by the invention is shown in FIG. 6. Advantageously, this record comprises a photograph 601 produced by an instant type camera, such as manufactured by the Polaroid Corporation. Quite satisfactory results are provided, for example, by the least expensive Polaroid model. The photographed image includes the wave forms produced on the CRT screen shown generally at 603, and the patient's name and date at 602 reproduced from the identifying mat film 505. A feature of the invention is that all such identification is easily permanently recorded on the photograph 601 without the necessity for any additional writing by the operator upon the record during or after the electrocardiogram or other medical procedure.

Figure 7A:
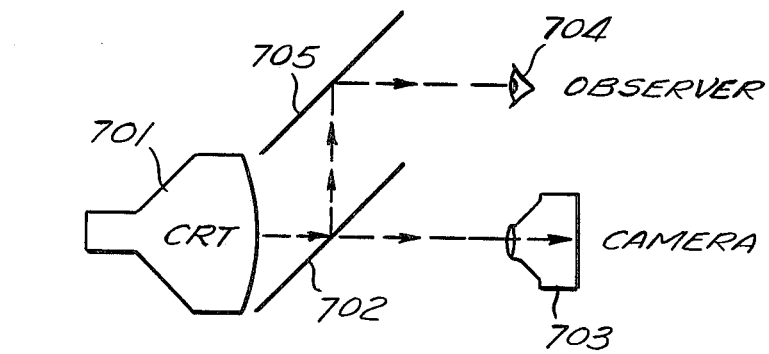
FIGS. 7A and 7B show alternative optic embodiments of the invention.

In addition to the optical wave paths shown in FIGS. 1 and 5, alternative embodiments may be provided in accordance with the present invention. Referring to FIG. 7A, the camera 703 is shown in line with the screen of the cathode ray tube 701 and obtains its information directly through a two-way mirror 702. The observer views the same image which is reflected from the two-way mirror 702 onto a second mirror 705. As shown, each of the mirrors 702 and 705 are set at a 45 degree angle with the cathode ray tube 701.

Figure 7B:
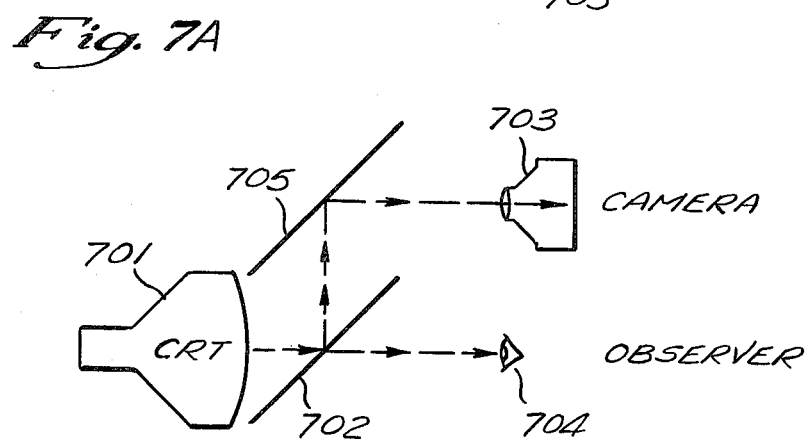

An embodiment which is a corollary of the embodiment of FIG. 7A is shown in FIG. 7B in which the observer views the image directly from the cathode ray tube through the two-way mirror 702 and the camera 703 views the image reflected off of mirror 705.

In the embodiments of FIGS. 7A and 7B, the camera and observer view the image which directly appears upon the face of the cathode ray tube. In the embodiments of FIGS. 7A and 7B therefore, the horizontal sweep of the cathode ray tube will be driven in its normal fashion, i.e., from left to right.

An important feature of the invention is that it provides for diagnostic instruments whose overall operation is quite simple. Thus, the only new step required of an operator experienced in using the prior art strip chart recorders is that of loading and removing pictures from an instant photographer or other type of camera. Since these cameras are in wide usage, the operation of the invention will be generally familiar to any nurse or technician skilled in taking electrocardiograms or other medical procedures. Moreover, the operator will find that the invention substantially facilitates performing these procedures by allowing for simultaneously viewing of the display upon the screen of the cathode ray tube, while photographing the displayed wave forms. Thus, the operator can be assured that the wave forms have the requisite quality and stability before and during exposure of the film. During the actual photographing sequence, there is no visual or other interruption of the visual display. In addition, the photographed image permanently records the patient's name, date and other information as written upon a transparent mat film 505.

Systems constructed in accordance with the present invention provide several additional significant advantages. The accuracy of the recorded display is very good, since the cathode ray tube provides for a wide bandwidth, ultralinear display and even an inexpensive camera accurately provides a permanent record containing all of the information necessary for recordation of voltages, currents, pressures, etc. recorded as a function of time including electrocardiographs, phonocardiographs, plethysmographs and rheographs. Various types of transducers may be employed with the invention including crystal, coppler and ultrasonic scanners.

What is claimed is:

1. A low cost, multi-channel recorder and display system for medical and other applications comprising:
    a cathode ray tube having vertical and horizontal deflection yokes;
    means coupled to said horizontal and vertical deflection yokes for simultaneously displaying plural wave forms corresponding to physiological phenomena on the screen of said cathode ray tube;
    optical channel means for simultaneously (i) continuously visually viewing the display upon the screen of said cathode ray tube and (ii) photographing said display without interrupting or affecting said visual display including:
        a two-way mirror mounted in front of said cathode ray tube and at a 45 degree angle therewith to provide both a reflected image and a through image of said display,
        a second mirror mounted at right angles to said two-way mirror in the path of said through image of said display,
        a camera mounted at right angles to the screen of said cathode ray tube in the path of said reflected image from said two-way mirror, and
        an operator window mounted in the optical path of the reflected image from said second mirror,
    removable means for inscribing the patient's name and other information to appear on the final photograph, comprising a transparent film mounted in the direct optic path of said camera at right angles to the screen of said cathode ray tube,
    means for illuminating said transparent film so that the image written thereon will be photographed simultaneously with the image being displayed on the screen of the cathode ray tube,
    an actuator button, and
    electronic control means responsive to said actuator button and the horizontal sweep signal applied to said horizontal deflection yoke for opening the camera shutter only at the beginning of a horizontal sweep and closing the shutter at the end of a single horizontal sweep, the shutter being so operated regardless of the timing of said actuator button.

2. The low cost, multi-channel recorder and display system described in claim 1 wherein said camera is a low cost, instant photography camera.

3. The low cost, multi-channel recorder and display system described in claim 1 further comprising
    a grey filter located at the end of said optical channel
    means for reducing the ambient light entering said optical channel.

4. The low cost, multi-channel recorder and display system described in claim 1 further comprising:
    an illuminated grid located in front of the screen of said cathode ray tube for providing an overlaid rectangular grid for the wave forms visually displayed and photographed by said system.

5. The low cost, multi-channel recorder and display system described in claims 1, 2, 3 or 4 wherein said electronic control means include means responsive to the blanking pulse produced when the beam is being returned after each sweep.

6. The low cost, multi-channel recorder and display system described in claim 1, wherein said transparent film has a mat finish so that information is easily written upon its surface.

7. A low-cost, multi-channel recorder and display system for medical and other applications comprising:
    a cathode ray tube oscilloscope for displaying physiological phenomena;
    means for simultaneously (i) continuously visually viewing the display upon the screen of said cathode ray tube and (ii) photographing said display without interrupting or otherwise affecting said visual display comprising:
        a two-way mirror mounted in front of said cathode ray tube to provide a reflected and a through image of said display,
        a second reflecting mirror mounted in the path of one of said through or reflected images of said display,
        a camera mounted in the path of one of said reflected or through images of said display, and an operator window mounted in the path of one of the other of said reflected or through images.

8. The low cost, multi-channel recorder and display system of claim 7, wherein said second mirror is mounted in the path of said through image, said camera is mounted in the path of the image reflected by said two-way mirror, and said operator window is mounted in the path of the image reflected from said second mirror.

9. The low cost, multi-channel recorder and display system of claim 7, wherein said second mirror is mounted in the path of said reflected image, said camera is mounted in the path of said through image, and said operator window is mounted in the path of the image reflected from said second mirror.

10. The low cost, multi-channel recorder and display system of claim 7, wherein said second mirror is mounted in the path of said reflected image, said operator window is mounted in the path of said through image, and said camera is mounted in the path of the image reflected from said second mirror.

11. The low cost, multi-channel recorder and display system of claims 7, 8, 9 or 10 including electronic control means responsive to the horizontal sweep of said oscilloscope and to an operator control means for opening the camera shutter only at the beginning of a horizontal sweep and closing the shutter at the end of a single horizontal sweep, the shutter being so operated regardless of the timing of said operator control means.

* * * * *